(12) United States Patent
Eilebrecht et al.

(10) Patent No.: US 9,277,882 B2
(45) Date of Patent: Mar. 8, 2016

(54) SENSOR FOR CONTACTLESS ELECTROCARDIOGRAPHIC MEASUREMENT

(71) Applicant: FORD GLOBAL TECHNOLOGIES, LLC, Dearborn, MI (US)

(72) Inventors: Benjamin Eilebrecht, Herne (DE); Jeroen Lem, Maastricht (NL); Marcel Mathissen, Wuerselen (DE); Achim Lindner, Euskirchen (DE); Rainer Vogt, Aachen (DE); Marian Walter, Aachen (DE); Steffen Leonhardt, Aachen (DE)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 14/466,421

(22) Filed: Aug. 22, 2014

(65) Prior Publication Data

US 2015/0057556 A1 Feb. 26, 2015

(30) Foreign Application Priority Data

Aug. 22, 2013 (DE) .......................... 10 2013 216 604

(51) Int. Cl.
| | |
|---|---|
| *A61B 5/18* | (2006.01) |
| *A47C 7/62* | (2006.01) |
| *A61B 5/04* | (2006.01) |
| *A61B 5/0408* | (2006.01) |
| *A61B 5/00* | (2006.01) |
| *B60N 2/44* | (2006.01) |
| *A61B 5/0205* | (2006.01) |
| *A61B 5/103* | (2006.01) |
| *B60N 2/00* | (2006.01) |
| *A61B 5/11* | (2006.01) |

(52) U.S. Cl.
CPC ... *A61B 5/18* (2013.01); *A47C 7/62* (2013.01); *A61B 5/02055* (2013.01); *A61B 5/0408* (2013.01); *A61B 5/04012* (2013.01); *A61B 5/04085* (2013.01); *A61B 5/1036* (2013.01); *A61B 5/6891* (2013.01); *A61B 5/6893* (2013.01); *A61B 5/721* (2013.01); *B60N 2/002* (2013.01); *B60N 2/44* (2013.01); *A61B 5/1115* (2013.01)

(58) Field of Classification Search
CPC ..... A61B 5/18; A61B 5/04012; A61B 5/6893
USPC .......................................................... 600/509
See application file for complete search history.

(56) References Cited

U.S. PATENT DOCUMENTS 5,957,854 A * 9/1999 Besson et al. ................. 600/509
7,684,854 B2 3/2010 Park et al.
(Continued)

FOREIGN PATENT DOCUMENTS

DE 102008049112 A1 5/2009
EP 2532306 A1 12/2012

*Primary Examiner* — Carl H Layno
*Assistant Examiner* — Jennifer Ghand
(74) *Attorney, Agent, or Firm* — Frank A. MacKenzie; Brooks Kushman P.C.

(57) ABSTRACT

A sensor for contactless electrocardiographic measurement on a person includes a carrier for mounting to a seat, an electrode for registering a measurement signal, a pressure sensor supporting the electrode on the carrier, and moisture and temperature sensors mounted to the carrier to detect conditions adjacent to the electrode and the subject person. The moisture sensor and the temperature sensor may be adjacent to at least one opening in the electrode. A processing unit receives information generated by the pressure sensor, the moisture sensor, and the temperature sensor, and filters the measurement signal based on the information. An acceleration sensor may also be mounted to the carrier and/or electrode and send signals to the processor.

14 Claims, 2 Drawing Sheets

(56) References Cited

U.S. PATENT DOCUMENTS

| | | | |
|---|---|---|---|
| 2006/0283652 A1* | 12/2006 | Yanai et al. | 180/272 |
| 2009/0284378 A1* | 11/2009 | Ferren et al. | 340/573.1 |
| 2011/0125002 A1* | 5/2011 | Ershov et al. | 600/384 |
| 2012/0238845 A1* | 9/2012 | Yang | 600/322 |
| 2013/0060120 A1* | 3/2013 | Futatsuyama et al. | 600/393 |
| 2014/0039330 A1* | 2/2014 | Seo et al. | 600/509 |

\* cited by examiner

SENSOR FOR CONTACTLESS ELECTROCARDIOGRAPHIC MEASUREMENT

CROSS-REFERENCE TO RELATED APPLICATIONS

This application claims foreign priority benefits under 35 U.S.C. §119(a)-(d) to DE 10 2013 216 604.4 filed Aug. 22, 2013, which is hereby incorporated by reference in its entirety.

TECHNICAL FIELD

The present invention relates to a sensor for contactless electrocardiographic measurement on a person. The invention furthermore relates to a sensor array equipped with a plurality of sensors, and to a seat or bunk equipped with a sensor array in a vehicle.

BACKGROUND

Measurement of the electrical potential, or electrical field strength, on the skin of a person by means of electrocardiographic sensors forms the basis of many medical diagnostic methods. In this way, for example, an electrocardiogram (ECG) may be recorded or the heart rate may be determined from the measured electrical potentials.

In conventional measurement methods for measuring the electrical potential on the skin, the latter is acquired by electrodes which are in direct electrical contact with the surface of the skin. An electrically conductive connection is thus established between the skin, on the one hand, and the electrode, on the other hand. In this case, however, it often proves difficult to ensure a sufficiently good electrical contact between the electrode and the skin, and therefore the body of the person being examined (the subject). Furthermore, the use of such diagnostic methods is also increasingly being provided in application fields in which direct access to the skin of the subject is not available, for example in vehicle applications for monitoring body functions and/or vital parameters of vehicle passengers on seats or bunks.

For example, U.S. Pat. No. 7,684,854 B2 discloses a sensor for contactless electrocardiographic measurement on a person. The person may in this case be on a stool, in a bed or on a vehicle seat. The electrocardiogram can be recorded from the body of the person wearing clothing without direct contact with the skin. The sensor comprises a flat electrically conductive electrode which comprises a measurement surface facing toward the person and a connection surface which faces away from the person, lies opposite the measurement surface and is electrically connected to a preamplifier. The electrode and the preamplifier of the sensor are enclosed by shielding.

Another contactless sensor for recording an electrocardiogram of a person is disclosed by EP 2 532 306 A1. The sensor comprises an electrically conductive electrode and a detection device, which is electrically connected to the electrode and is configured in order to amplify the signals received by the electrode. The sensor is intended to be arranged in a vehicle seat and to determine particular physiological parameters of a driver sitting on the vehicle seat.

DE 20 2012 001 096 U1 discloses capacitive sensors for capacitive recording of vital parameters of a driver of a vehicle. To this end, the sensors are fitted in or on the backrest of the seat of the vehicle. In particular, according to one embodiment it is proposed to arrange the sensors in or on the backrest of the seat while being distributed in two rows separated by a distance corresponding to the width of the spinal column of the driver. In each row, the sensors, with an area of from 16 to 36 cm$^2$, are arranged at equal distances of from 1 to 5 cm from one another. In another embodiment, instead of the two separate sensor rows with sensors distributed over the entire height of the seat at a distance of 1-5 cm, two membrane sensors with a width of from 4 to 10 cm are arranged over the entire seat height with a separation corresponding to the spinal column.

Furthermore, DE 10 2008 049 112 A1 discloses a capacitive textile electrode for measuring body functions and/or vital parameters of persons for vehicle applications, for example in a seat or a bunk, which electrode has a multilayer structure. This comprises two textile layers, each of which has an electrically conductive electrode region, a further textile layer being provided in order to establish a distance between the other two textile layers.

In general, contactless electrocardiographic measurement is distinguished in that there may, for example, be clothing between the skin of the subject and the electrode of the sensor. The signal quality of a measurement signal registered in this way by the electrode may, however, be substantially influenced by various factors. Such factors may include, for example, the vibrations to which the sensor is exposed at the time of the measurement, the contact pressure which exists between the subject and the electrode at the time of the measurement, the microclimate between the electrode and the skin of the subject, the materials of the clothing, as well as the electrostatic charge in the vicinity of the electrode.

SUMMARY

Against this background, it is the object of the present invention to provide a sensor, a sensor array, and a seat or a bunk, for contactless electrocardiographic measurement on persons, preferably in vehicle applications, with which reliable information can be obtained about the body functions and/or vital parameters of the person, that is to say they are capable of delivering a reliable signal with good signal quality at any time.

It should be pointed out that the features individually mentioned in the claims may be combined with one another in any technically expedient way, and represent further configurations of the invention. The description additionally characterizes and specifies the invention particularly in connection with the figures.

According to a disclosed embodiment, a sensor for contactless electrocardiographic measurement on a person, preferably in vehicle applications, comprises a flat carrier for fastening the sensor on an object, and at least one flat electrically conductive electrode opposite and connected to the carrier. In the context of the present invention, "contactless" is to be understood as meaning that the electrode does not directly touch the skin of the subject. For example, articles of clothing may be arranged between the subject's skin and the electrode.

In the disclosed sensor, the electrode is supported on the carrier by at least one pressure sensor. A moisture sensor, a temperature sensor and an acceleration sensor are furthermore arranged between the carrier and the electrode. The aforementioned sensor types may therefore be integrated in the sensor, making it possible to record all essential parameters for each individual sensor when carrying out the electrocardiographic measurement on a person. Furthermore, information can be obtained about the quality and therefore the usability of the measurement signal registered by the electrode of the sensor. The measurement signal may, for example, be suppressed if the signal quality is too low, so that false conclusions are drawn in relation to the body functions and/or vital parameters of the subject. Accordingly, more reliable information about the body functions and/or vital parameters of the person can be obtained with the aid of the disclosed sensor.

An advantageous configuration of the invention provides a processing unit configured to receive information generated by the pressure sensor, the moisture sensor, the temperature sensor and the acceleration sensor, and to filter a measurement signal registered by the electrode according to the information received. In this way, the signal quality of the registered measurement signal can be improved, for example by artefacts generated because of the parameters during the measurement being filtered out of the measurement signal.

In another advantageous configuration, the various sensor signals, generated multiply in parallel, are used in order to eliminate or compensate for undesired signal components, highlight the desired signal components and/or adapt the transfer properties of the electronics and the subsequent signal processing with the aid of the measured information.

According to another advantageous configuration of the invention, an opening in the electrode is respectively provided opposite the moisture sensor and the temperature sensor. This facilitates determination of the microclimate between the electrode and the skin of the subject, by determining the moisture content of the clothing worn by the person.

A sensor array according to the invention comprises at least two sensors of the above-described type. Any type of arrangement of a plurality of these sensors is to be understood as a sensor array in the sense of the present invention.

According to the present invention, a seat or a bunk in a vehicle has at least one sensor array according to the above-described type according to the invention for contactless electrocardiographic measurement on a person who is on the seat or bunk.

Further features and advantages of the invention may be found in the following description of exemplary embodiments of the invention, which are not to be interpreted as restrictive and will be explained in more detail below with reference to the drawing. In this drawing, schematically:

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In the various figures, parts which are the same are always provided with the same references, so that they will also generally only be described once.

Figure 1:
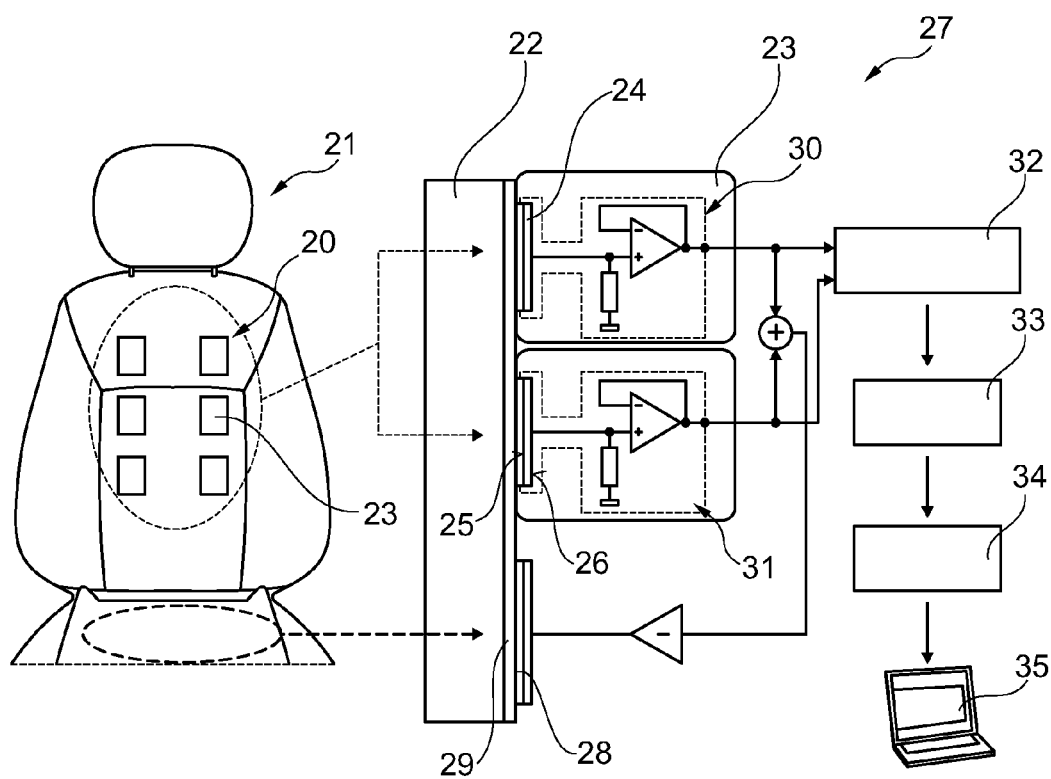
FIG. 1 shows a sensor array and a seat for a vehicle, according to the prior art.

FIG. 1 schematically represents a sensor array 20 and a seat 21 for a vehicle for contactless electrocardiographic measurement on a person or subject 22, according to the prior art. As can be seen, the sensor array consists of a matrix arrangement of six sensors 23 arranged in a 3×2 matrix in a backrest of a vehicle seat, each of which sensors comprises a flat electrically conductive electrode 24. Another electrode, via which a reference potential is applied to the circuit, is furthermore arranged in the seat surface of the vehicle seat 21.

Each electrode 24 comprises a measurement surface 25 facing toward the subject 22, and a connection surface 26, facing away from the person and opposite the measurement surface 25, for the connection of a measuring device 27. As represented in FIG. 1, the measurement surface 25 of the individual electrodes 24 does not directly touch the skin of the subject 22. Rather, insulation 28 is applied on the measurement surface 25 of each electrode 24 in FIG. 1. Furthermore, the clothing 29 worn by the subject person also lies between the subject 22 and the measurement surface 25.

The measuring device 27 represented in FIG. 1 comprises one preamplifier 31, enclosed by shielding 30, per sensor 23. Furthermore, an instrument amplifier 32 amplifies the measurement signal registered by the electrodes 24 of the sensors 23, followed by a filtering and amplification unit 33 as well as an A/D converter 34. The digital measurement signal output by the A/D converter 34 may then be processed further in a suitable way, for example by means of a digital computer unit 35.

Figure 2:
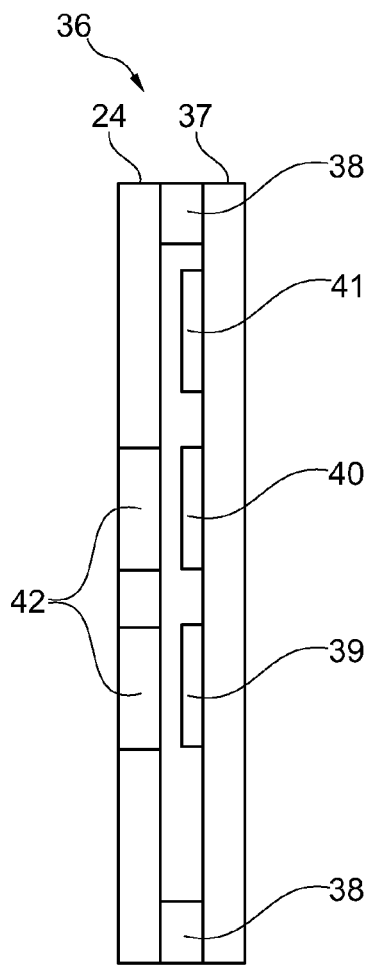
FIG. 2 shows a lateral cross-sectional view of a sensor according to an embodiment of the invention.
Figure 3:
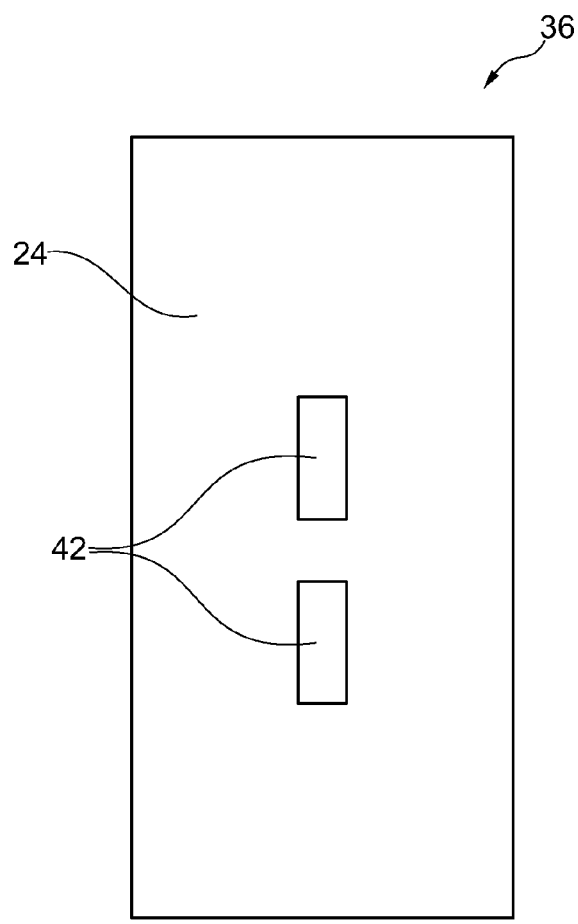
FIG. 3 shows a front view of the sensor of FIG. 2.

FIG. 2 schematically represents a lateral cross-sectional view of a sensor 36 according to an embodiment of the invention. FIG. 3 represents the same sensor 36 in a front view. The sensor 36 comprises a flat carrier 37 for fastening the sensor 36 on an object, for example a backrest of a vehicle seat, and furthermore a flat electrically conductive electrode 24 opposite and connected to the carrier 37.

Furthermore, in the sensor represented in FIG. 2, two pressure sensors 38, a moisture sensor 39, a temperature sensor 40 and an acceleration sensor 41 are arranged between the carrier 37 and the electrode 24. In particular, the electrode 24 is supported on the carrier 37 by means of the two pressure sensors 38, so that a contact pressure between the electrode 24 and the subject can be acquired with the aid of the pressure sensors 38.

As can furthermore be seen in FIGS. 2 and 3, an opening 42 in the electrode 24 is respectively provided opposite the moisture sensor 39 and the temperature sensor 40, in order to make it possible for the moisture sensor 39 and the temperature sensor 40 to determine a microclimate between the electrode 24 and the skin of the subject, in particular the moisture content of the clothing worn by the person.

A processing unit (not represented in FIGS. 2 and 3, but refer to FIG. 1) is configured to receive the information generated by the pressure sensor 38, the moisture sensor 39, the temperature sensor 40 and the acceleration sensor 41, and to filter a measurement signal acquired by the electrode 24 according to the information received, in particular to filter any artefacts (which may be generated because of the parameters during the measurement) out of the measurement signal and therefore substantially improve the signal quality of the measurement signal, so that reliable information about the body functions and/or vital parameters of the subject can be obtained.

The sensor according to the invention, the sensor array and the seat or bunk have been explained in more detail with the aid of an exemplary embodiment represented in the figures. The sensor, the sensor array and the seat or bunk are not however restricted to the embodiment described herein, but also comprise further embodiments acting in the same way. For instance, it is conceivable, for example, for further external sensors, for example sensors for detecting light radiation and/or heat radiation, to also be connected to the processing unit, in addition to the pressure, moisture, temperature and acceleration sensors integrated into the sensor according to the invention.

In a preferred embodiment, the sensor according to the invention, the sensor array and the seat or the bunk are used for contactless electrocardiographic measurement on a person in a vehicle, in particular a motor vehicle.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A contactless electrocardiographic sensor, comprising:
   a carrier for mounting to an object;
   an electrode attached to the carrier;
   a pressure sensor disposed to detect pressure between the electrode and the carrier; and
   a moisture sensor and a temperature sensor mounted to at least one of the carrier and the electrode and adjacent to at least one opening in the electrode.

2. The sensor of claim 1, further comprising a processing unit receiving information generated by the pressure sensor, the moisture sensor, and the temperature sensor, and filtering a measurement signal registered by the electrode based on the information.

3. The sensor of claim 2, wherein the processing unit utilizes the information to at least one of: a) eliminate an undesired component of the measurement signal; b) compensate for an undesired component of the measurement signal; c) highlight a desired component of the measurement signal; and d) adapt transfer properties of subsequent signal processing.

4. The sensor of claim 1, further comprising an acceleration sensor.

5. The sensor of claim 1, wherein the pressure sensor supports the electrode on the carrier.

6. The sensor of claim 1, wherein the moisture sensor is adjacent to a first opening in the electrode and the temperature sensor is adjacent to a second opening in the electrode.

7. A contactless electrocardiographic sensor, comprising:
   a carrier for mounting to a seat;
   an electrode for registering a measurement signal;
   a pressure sensor supporting the electrode on the carrier;
   a moisture sensor and a temperature sensor mounted to the carrier adjacent to at least one opening in the electrode; and
   a processing unit filtering information generated by the pressure sensor, the moisture sensor, and the temperature sensor, based on the information.

8. The sensor of claim 7, wherein the processing unit utilizes the information to at least one of: a) eliminate an undesired component of the measurement signal; b) compensate for an undesired component of the measurement signal; c) highlight a desired component of the measurement signal; and d) adapt transfer properties of subsequent signal processing.

9. The sensor of claim 7, further comprising an acceleration sensor.

10. The contactless electrocardiographic sensor of claim 7, wherein the moisture sensor is adjacent to a first opening in the electrode and the temperature sensor is adjacent to a second opening in the electrode.

11. A seat for a motor vehicle having a sensor array for contactless electrocardiographic measurement, the sensor array comprising:
    a carrier mounted to the seat;
    an electrode for registering a measurement signal;
    a pressure sensor supporting the electrode relative to the carrier;
    a moisture sensor and a temperature sensor mounted to the carrier adjacent to at least one opening in the electrode to detect conditions adjacent to a measuring surface of the electrode; and
    a processing unit receiving information generated by the pressure sensor, the moisture sensor, and the temperature sensor, and filtering the measurement signal based on the information.

12. The seat of claim 11, wherein the processing unit utilizes the information to at least one of: a) eliminate an undesired component of the measurement signal; b) compensate for an undesired component of the measurement signal; c) highlight a desired component of the measurement signal; and d) adapt transfer properties of subsequent signal processing.

13. The seat of claim 11, wherein the sensor array further comprises an acceleration sensor mounted to at least one of the carrier and the electrode, and the processing unit further receives information generated by the acceleration sensor.

14. The seat of claim 11, wherein the moisture sensor is adjacent to a first opening in the electrode and the temperature sensor is adjacent to a second opening in the electrode.

* * * * *